(12) United States Patent
Barbour

(10) Patent No.: US 7,576,853 B2
(45) Date of Patent: Aug. 18, 2009

(54) ELECTRONICALLY MODULATED DYNAMIC OPTICAL PHANTOMS FOR BIOMEDICAL IMAGING

(75) Inventor: Randall L. Barbour, Glen Head, NY (US)

(73) Assignee: The Research Foundation of State University of New York, Albany, NY (US)

( * ) Notice: Subject to any disclaimer, the term of this patent is extended or adjusted under 35 U.S.C. 154(b) by 358 days.

(21) Appl. No.: 11/451,233

(22) Filed: Jun. 12, 2006

(65) Prior Publication Data

US 2007/0004026 A1 Jan. 4, 2007

Related U.S. Application Data

(60) Provisional application No. 60/689,248, filed on Jun. 10, 2005.

(51) Int. Cl.
*G02B 23/10* (2006.01)
(52) U.S. Cl. .................. 356/243.1; 250/252.1
(58) Field of Classification Search ............. 356/243.1; 250/252.1
See application file for complete search history.

(56) References Cited

U.S. PATENT DOCUMENTS

| | | | |
|---|---|---|---|
| 3,597,044 A | 8/1971 | Castellano | |
| 4,184,768 A | 1/1980 | Murphy et al. | |
| 4,338,821 A | 7/1982 | Dion | |
| 5,030,005 A * | 7/1991 | Swope et al. ............. | 356/243.1 |
| 5,416,575 A | 5/1995 | Schwartz et al. | |
| 6,529,846 B2 | 3/2003 | Barbour et al. | |
| 6,549,284 B1 | 4/2003 | Boas et al. | |
| 6,770,068 B2 | 8/2004 | Ruiz et al. | |
| 6,795,195 B1 | 9/2004 | Barbour et al. | |
| 2005/0145786 A1 | 7/2005 | Rice et al. | |

FOREIGN PATENT DOCUMENTS

EP  0 268 488 B1  5/1988

* cited by examiner

*Primary Examiner*—Roy Punnoose
(74) *Attorney, Agent, or Firm*—Scully, Scott, Murphy & Presser, P.C.

(57) ABSTRACT

A method and system for calibrating an optical tomographic imaging system that is configured to execute time-series optical measurements of a target's response to incident optical energy is presented. An electro-active device that is configured to be electronically modulated to control the electro-active device's opacity is embedded in a dense scattering medium. A known hemodynamic response pattern is selected and at least one wavelength of optical energy that produces the known hemodynamic response pattern is determined. A wavelength-dependent driving voltage function is then computed. A voltage is then applied to the electro-active device according to the wavelength-dependent driving voltage function. Optical energy is then transmitted to the scattering medium at the at least one wavelength and a hemodynamic response for the target is determined. The known hemodynamic response pattern and the determined hemodynamic response pattern are then compared.

18 Claims, 10 Drawing Sheets

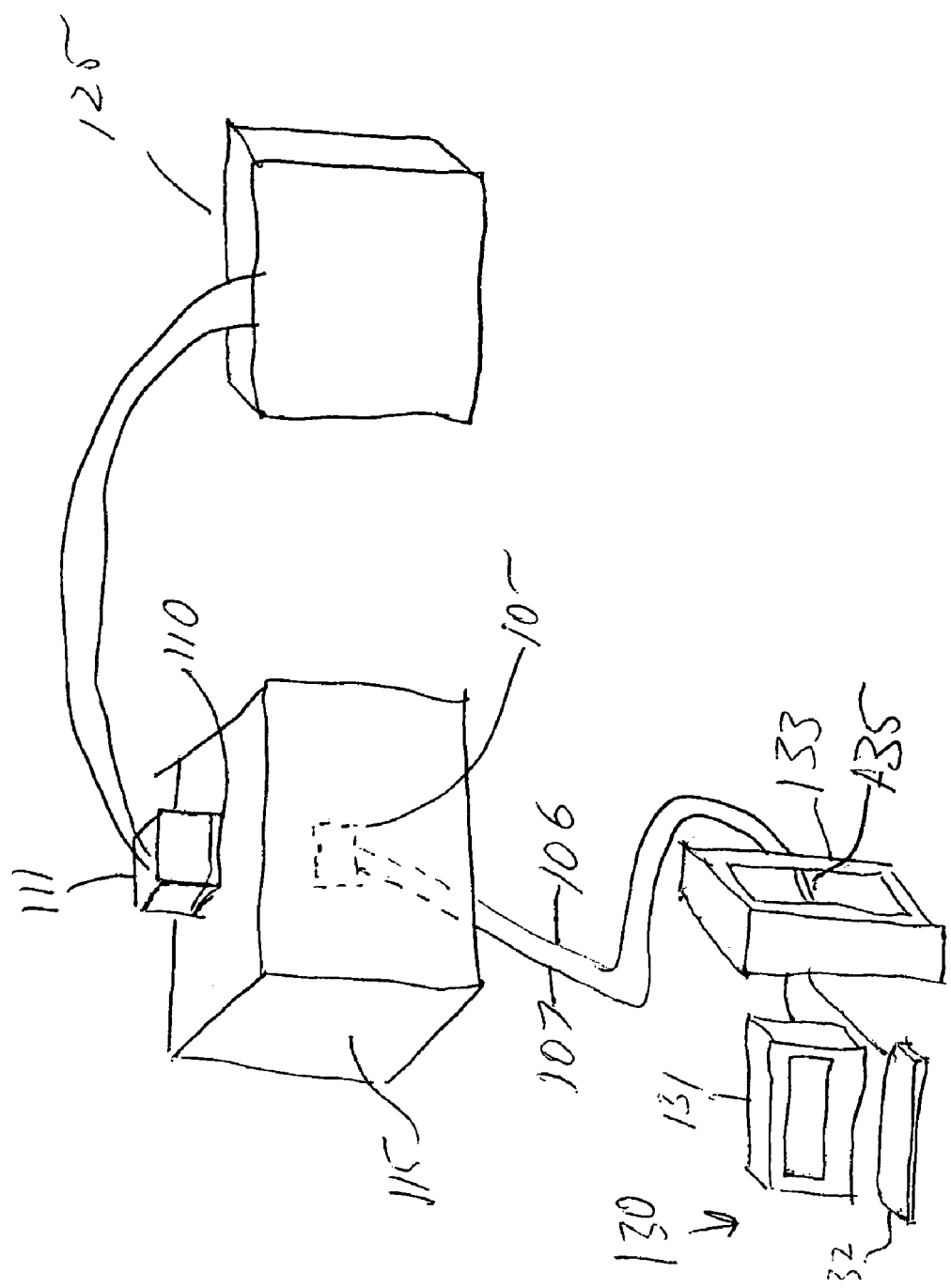

Figure 3. Modeled response to cuff ischemia, and measured response to three consecutive trials using EC cell.

- Scalp
- Skull
- Muscle
- CSF
- Gray Matter
- White Matter
- ○ Source/Detector

ELECTRONICALLY MODULATED DYNAMIC OPTICAL PHANTOMS FOR BIOMEDICAL IMAGING

CROSS REFERENCE TO RELATED CASES

This claims priority to and the benefit of Provisional U.S. Patent Application Ser. No. 60/689,248, filed Jun. 10, 2005, the entirety of which is incorporated herein by reference

TECHNICAL FIELD

The invention relates generally to biomedical optical devices, and more particularly to systems for, and methods of, calibrating biomedical optical devices.

BACKGROUND INFORMATION

Biomedical optical devices are increasingly being used to quantitatively analyze the optical properties of living tissue. In one application domain, devices are being used to produce tomographic images of the bulk optical properties of large tissue structures. As with other imaging technologies, their practical use requires the availability of a calibration mediums (i.e., phantoms) that serve to calibrate and quantify system performance.

Because of the recent introduction of systems capable of generating an image time-series, a need has arisen for phantoms whose optical properties can be suitably varied in ways that mimic the temporal variations of tissue optical properties, such as those produced by changes in vascular reactivity or oxidative demand that result in optical changes that are wavelength-dependent., for example.

One approach that has been reported as a means to measure dynamic states (time-varying states) is the use of elastomeric materials containing chromagens of interest. The internal volume or concentration of chromagen is varied in time (Schmitz et al., Applied Optics, 39, 6466-6486, 2000). For example, latex balloons are filled with a dilute hemoglobin solution and attached to a piston pump that serves to vary its internal volume. Detection of transmitted or reflected light having passed through a scattering medium containing such inclusions produces a time-varying optical signal. In principle this approach can be extended to include multiple inclusions, each controlled separately and differing in the concentration or composition of a chromagen. In situations wherein it is desirable to mimic complex dynamic states of tissue, a system of this sort invariably requires use of complex fluidic control devices. More desirable would be to employ materials or devices with optical properties that can be electrically modulated.

One well-known device class having this property is acoustic-optical cells. These devices however, employ bulky support mechanics that can attenuate the incident optical field. These devices and also require an incident acoustic field.

SUMMARY OF THE INVENTION

The invention relates generally to biomedical optical devices, and more particularly to systems for, and methods of, calibrating biomedical optical devices.

In one aspect, the invention involves a method of calibrating an instrument configured to execute time-series energy measurements of a target's response to incident energy. The method includes providing an electro-active device that is configured to be electronically modulated to control the electro-active device's opacity. The electro-active device is embedded in a dense scattering medium. The method further includes selecting, for the target, a known time-dependent response pattern and at least one associated coefficient value corresponding to a known physical property, determining at least one wavelength of energy that produces the known time-dependent response pattern for the known physical property of the target, and computing a wavelength-dependent driving voltage function by normalizing the at least one wavelength to a voltage response of the electro-active device. The method further includes applying a voltage to the electro-active device according to the wavelength-dependent driving voltage function to electrically modulate the electro-active device and thereby vary the opacity of the electro-active device, and synchronizing the instrument with the wavelength-dependent voltage driving function. The method still further includes transmitting energy at the at least one wavelength to the scattering medium and receiving scattered energy from the scattering medium, determining, based on the received scattered energy, a time-dependent response pattern for the target, and comparing the known time-dependent response pattern and the determined time-dependent response pattern.

In some embodiments, the energy includes optical energy or acoustic energy. In other embodiments, the electro-active device includes a twisted nematic liquid crystal or an electro-chromic polymer. In one embodiment, the twisted nematic liquid crystal includes a dye coating to vary the optical properties of light transmitted through the liquid crystal. In still another embodiment, the dense scattering medium is human tissue.

In another aspect, the invention involves a method of calibrating an optical tomographic imaging system that is configured to execute time-series optical measurements of a target's response to incident optical energy. The method includes providing an electro-active device that is configured to be electronically modulated to control the electro-active device's opacity. The electro-active device is embedded in a dense scattering medium. The method further includes selecting, for the target, a known hemodynamic response pattern and at least one associated coefficient value corresponding to a known optical property of the target, determining at least one wavelength of optical energy that produces the known hemodynamic response pattern for the known optical property of the target, and computing a wavelength-dependent driving voltage function by normalizing the at least one wavelength to a voltage response of the electro-active device. The method still further includes applying a voltage to the electro-active device according to the wavelength-dependent driving voltage function to electrically modulate the electro-active device and thereby vary the opacity of the electro-active device, and synchronizing an image framing rate of the optical tomographic imaging system with the wavelength-dependent voltage driving function. The method yet further includes transmitting optical energy at the at least one wavelength to the scattering medium and receiving scattered optical energy from the scattering medium, determining, based on the received scattered optical energy, a hemodynamic response for the target, and comparing the known hemodynamic response pattern and the determined hemodynamic response pattern.

In some embodiments, the electro-active device includes a twisted nematic liquid crystal or an electro-chromic polymer. In another embodiment, the twisted nematic liquid crystal includes a dye coating to vary the optical properties of light transmitted through the liquid crystal. In one embodiment, the dense scattering medium is human tissue.

In still another aspect, the invention involves a system of calibrating an optical tomographic imaging system that is configured to execute time-series optical measurements of a target's response to incident optical energy. The system includes an electro-active device that is configured to be electronically modulated to control the electro-active device's opacity. The electro-active device is embedded in a dense scattering medium. The system further includes means for selecting, for the target, a known hemodynamic response pattern and at least one associated coefficient value corresponding to a known optical property of the target, means for determining at least one wavelength of optical energy that produces the known hemodynamic response pattern for the known optical property of the target, and means for computing a wavelength-dependent driving voltage function by normalizing the at least one wavelength to a voltage response of the electro-active device. The system still further includes means for applying a voltage to the electro-active device according to the wavelength-dependent driving voltage function to electrically modulate the electro-active device and thereby vary the opacity of the electro-active device, and means for synchronizing an image framing rate of the optical tomographic imaging system with the wavelength-dependent voltage driving function. The system still further includes means for transmitting optical energy at the at least one wavelength to the scattering medium and receiving scattered optical energy from the scattering medium, means for determining, based on the received scattered optical energy, a hemodynamic response for the target, and means for comparing the known hemodynamic response pattern and the determined hemodynamic response pattern.

In some embodiments, the electro-active device includes a twisted nematic liquid crystal or an electro-chromic polymer. In another embodiment, the twisted nematic liquid crystal includes a dye coating to vary the optical properties of light transmitted through the liquid crystal. In one embodiment, the dense scattering medium is human tissue.

In yet another aspect, the invention involves a program storage device readable by a machine, tangibly embodying a program of instructions executable by the machine to perform method steps for calibrating an optical tomographic imaging system that is configured to execute time-series optical measurements of a target's response to incident optical energy. The method steps include providing an electro-active device that is configured to be electronically modulated to control the electro-active device's opacity. The electro-active device is embedded in a dense scattering medium. The method steps further include selecting, for the target, a known hemodynamic response pattern and at least one associated coefficient value corresponding to a known optical property of the target, determining at least one wavelength of optical energy that produces the known hemodynamic response pattern for the known optical property of the target, and computing a wavelength-dependent driving voltage function by normalizing the at least one wavelength to a voltage response of the electro-active device. The method steps still further include applying a voltage to the electro-active device according to the wavelength-dependent driving voltage function to electrically modulate the electro-active device and thereby vary the opacity of the electro-active device, and synchronizing an image framing rate of the optical tomographic imaging system with the wavelength-dependent voltage driving function. The method steps yet further include transmitting optical energy at the at least one wavelength to the scattering medium and receiving scattered optical energy from the scattering medium, determining, based on the received scattered optical energy, a hemodynamic response for the target, and comparing the known hemodynamic response pattern and the determined hemodynamic response pattern.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1C is an illustrative block diagram of a set-up for calibrating a biomedical imaging device using electronically modulated dynamic optical phantoms, according to one embodiment of the invention.

DESCRIPTION

Figures 1A, 1B:
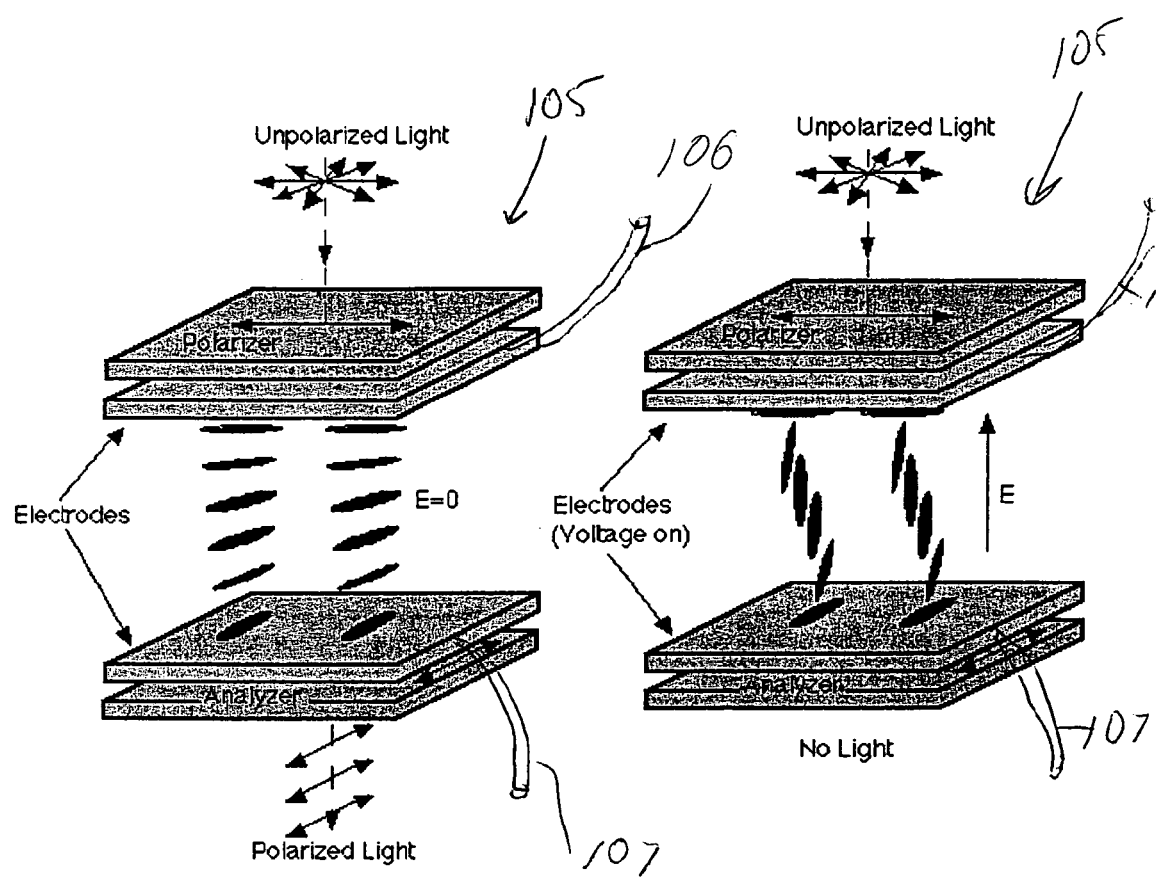
FIGS. 1A and 1B are illustrative schematic diagrams of a compact device including electro-active materials, according to one embodiment of the invention.

The present invention involves using compact devices including electro-active or electro-modulatable materials, or thin films, that can be embedded in a dense scattering media, such as silicon rubber with added $TiO_2$ to act as a scatter, Intralipid, opaque plastics such as white Delrin, or Teflon, for example. With application of an electrical source, the time dependence of the optical properties of the device can be altered in definable ways. As shown in FIG. 1, an exemplary compact device (e.g., twisted nematic liquid crystal) 105 includes small diameter electrical leads 106, 107. Nearly the entire surface of the compact device 105 can be optically active and can be easily and rapidly modulated using an external power source (not shown). In one embodiment, the present invention includes a device employing a liquid crystal (LC) cell (e.g. device 105 of FIGS. 1A and 1B) that attenuates an incident optical field either by absorption or scattering of light. Normally, LCs are not particularly wavelength selective and instead serve as broadband attenuators, thus potentially limiting their utility to mimic complex biological responses.

LC attenuating properties also depend on the incident radiation's angle of incidence and therefore using such devices in a scattering medium might pose a challenge to easily defining the expected attenuation. Despite these concerns, an approach that can overcome these difficulties is described hereinbelow.

In another embodiment, the invention includes electrochromic (EC) polymers, which offer potentially greater flexibility in the ability to mimic complex responses and are more reliable. EC polymers are a broad and expanding class of materials (see review by Argun et al. Chem. Mater., 16, 4401-4412, 2004) that have optical properties that are sensitive to an applied electric field. In this embodiment, a particular EC material is added to suitable polymers or support vessels to provide a convenient means to vary the local spectral properties of a dense scattering medium.

In still another embodiment, the invention involves nanoscale optical components. These components employ subwavelength grating structures that enable them to function as a wavelength-dependent attenuator. In practice, a medium, such as silicon rubber, doped with a scatterer, such a titanium dioxide, with or without added dye, could contain one or more inclusions of this sort. Each of the nano-scale optical components is electronically modulated. The details of the electrical modulation could be simple or complex and could contain a range of spectrally sensitive EC materials.

In yet another embodiment, a phantom vessel containing such inclusions (electro-active devices) could be molded in the shape of various anatomical structures (e.g. head, breast, limb, torso, small animals, etc.), each containing a range of LC and/or EC materials. Devices of this sort could thus serve as a quantitative means to assess the accuracy of image recovery algorithms and for quantifying the performance (accuracy and precision) of optical tomographic imaging systems or as an objective means to determine the detectability and quantifiability of a disease processes that influences the temporal-spectral properties of tissue.

Appropriate EC and/or LC materials include those materials that absorb or scatter optical energies, or produce luminescence or fluorescence fields, and possess optical properties that respond to an applied electric field.

Appropriate nano-devices include any nano-scale optical device that employs gratings on a sub-wavelength scale.

Appropriate optical tomographic systems include systems using any optical source, and any optical detector in any arrangement or geometry for any target medium.

Appropriate dense scattering mediums include any medium that scatters incident optical energy.

Referring to FIGS. 1A-C, in one embodiment, an adjustable measuring head 111 of an optical tomographic imaging system 125 that allows for surface contact between an array of optical fibers 110 and a dense scattering target medium 115 containing LC cell(s) 105 (provided by LC TEC Displays, Borlänge Sweden) is used to collect a time series of optical array measurements. The optical tomographic imaging system 125 provides for time-multiplexed, multi-wavelength source illumination and parallel multi-channel light detection with adaptive gain control.

These optical measurements can be accomplished using an illumination-detection scheme that is based on detection of CW, frequency- or time-domain data. In the preferred embodiment, the optical tomographic imaging system 125 employed is the DYNOT Imaging System (Model 232 CW) commercially available from NIRx Medical Technologies, Glen Head, N.Y.

Control of the LC cell(s) 105 is achieved using a LabView control program she LabView control program serves to modulate voltage applied to the LC cells(s) 105. The LabView control program resides and executes on a typical computer system 130, which includes a monitor 131, keyboard 132, and CPU chassis 133. The central processing unit (CPU) chassis 133 houses one or more processors, memory such as random access memory, and a storage device such as a hard disk. The voltage is supplied by a National Instruments Data Acquisition Card (model no. 6715E) 135, which resides in the CPU chassis 133. The opacity of the LC cell(s) 105 is varied by amplitude modulating over a range of ±10 V by a voltage carrier signal operating in the 10-1000 Hz range, which is supplied by the Data Acquisition Card 135 via the wires 106 and 107. Use of an AC carrier serves to maximize the stability and lifetime of the LC cell(s) 105.

The time-dependence of the amplitude modulation of the LC cell(s) 105 serves as the basis for mimicking the desired time-varying optical signal (e.g., a hemodynamic response). This mimicry is accomplished by synchronizing the image frame acquisition of the optical tomographic imaging system 125 to changes in the opacity of the LC cell(s) 105. Thus, for example, for each image frame of the time-series the opacity of the LC cell(s) 105 is adjusted to correspond to all measurement wavelengths' contributions to the optical signal. In the case of a two-wavelength measurement, a pair of image frames is collected (one for each wavelength) for each time point corresponding to the optical signal time series. This paired measurement scheme is repeated for each successive time point associated with the optical signal time series such that at each time point there is a corresponding adjustment in the wavelength-dependent LC cell opacity. A similar scheme would hold for a three or more wavelength measurement scheme, with appropriate adjustments made for the wavelength-dependent time multiplexing of the image frames.

The described measurement scheme leads to an oversampling of optical measures, such that, in the case of a two-wavelength measurement, only half of the optical measures actually are used to recover the programmed optical properties of the LC cell(s) 105 that correspond to the desired optical signal time series. This oversampling approach is taken only as a matter of convenience, as the considered optical tomographic imaging system 125 provides for simultaneously multi-wavelength illumination. Explicitly, when the opacity of the LC cell(s) 105 is adjusted for the desired response for one-wavelength, data simultaneously collected at the other measuring wavelength is ignored. Upon the next image frame, the opacity of the LC cell(s) 105 is adjusted for the other measuring wavelength and data simultaneously collected using the first measuring wavelength is ignored. Thus, for each pair of image frames a total of four wavelengths measurements is collected, of which half are used to recover the desired optical signal time series.

Figure 2:
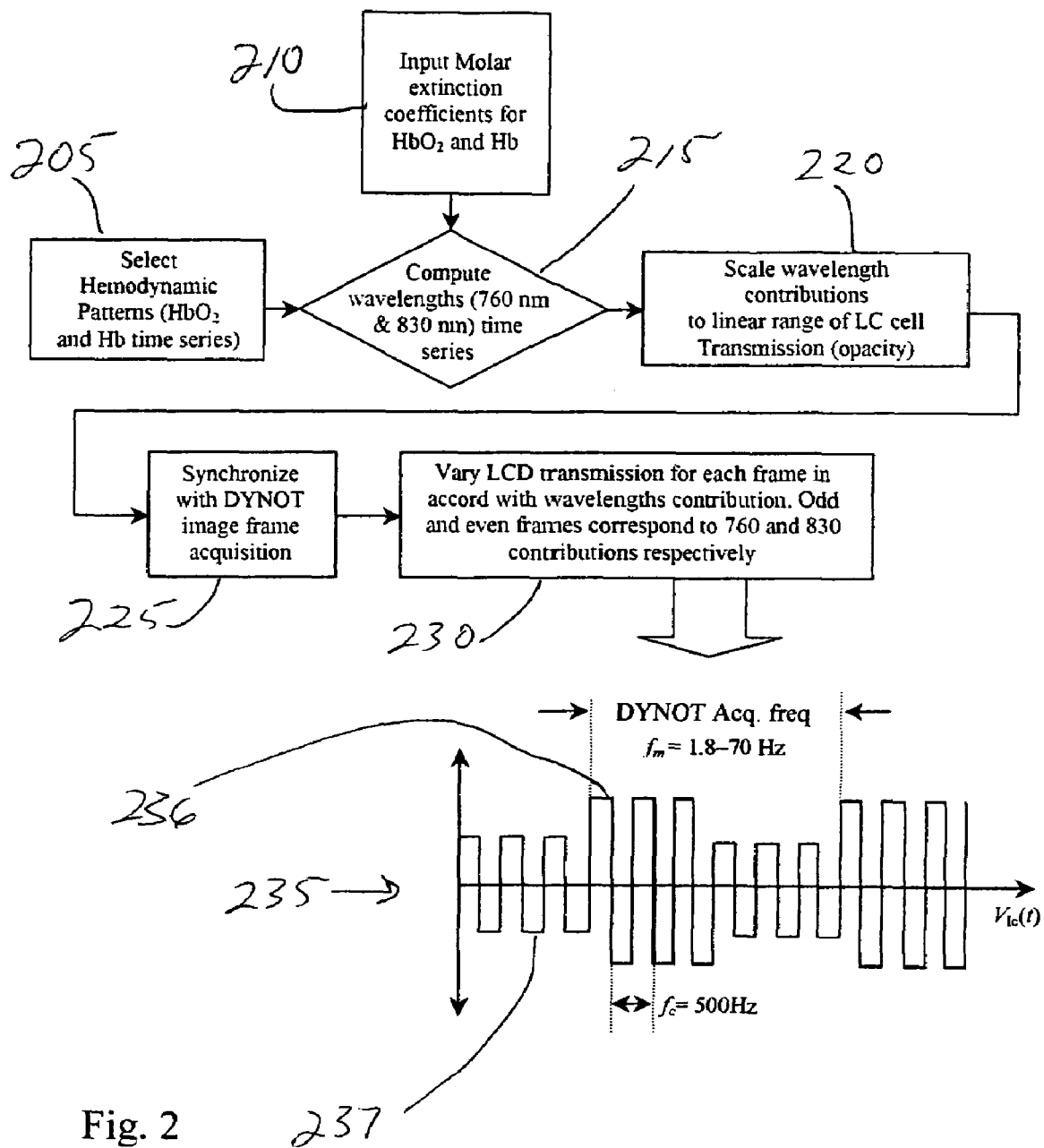
FIG. 2 is an illustrative flow diagram of a method for electronically modulating dynamic optical phantoms for calibrating a biomedical imaging device, according to one embodiment of the invention.

Referring to FIG. 2, in one embodiment, a flow diagram of a method for electronically modulating dynamic optical phantoms for biomedical imaging is shown. The sequence of operations that are performed in "programming" the phantom to mimic the desired physiological response are detailed below.

A hemodynamic time series is selected that will serve as the basis for computation of the wavelength-dependent driving functions that are used to control the LC cell(s) 105 opacity (Step 205). In the exemplary cases described in detail hereinbelow, oxy- and deoxy-hemoglobin time series that were calculated from actual human-subjects measurements made at 760 and 830 nm were chosen. Molar extinction coefficients are then selected (Step 210). Molar extinction coefficients are coefficient values of the optical properties of a particular scattering medium.

The wavelength contributions that represent the hemodynamic time series are computed using the Beer-Lambert Law or other suitable algebraic transform [C. H. Schmitz et al., "Design and implementation of dynamic near-infrared optical tomographic imaging instrumentation for simultaneous dual-breast measurements," Applied Optics 44:2140-2153 (2005).] (Step 215). By using an established physics model for the dependence of each wavelength's absorption coefficient $\mu_a$ on the tissue chromophore-concentrations, the $\mu_a$ time series is computed that would have to exist in a hypothetical unit-thickness or unit-volume of tissue in order to reproduce the hemodynamic model function. Then, using a theoretical model (e.g., diffusion equation) for the dependence of measured light intensities on absorption strength, the time-varying measurement that the hypothetical tissue would have to produce if its $\mu_a$ varied in the computed manner is determined.

The maximum and minimum values of the functions calculated in step 215 are normalized (scaled) to a desired voltage response range of the LC cell(s) 105 (e.g. 1.5v (clear) to 3.0v (opaque)), thereby establishing desired wavelength-dependent driving voltage functions to control the time varying opacities of the LC cell(s) 105 (Step 220).

The wavelength-dependent driving voltage functions computed in step 220 are synchronized with the image framing rate of the optical tomographic imaging system 125 to allow for the collection of a pair of image frames for each time point in the wavelength-dependent driving voltage function time series (Step 225). For each image frame captured, the LC cell opacity, defined by the wavelength-dependent driving function, is held constant during the time needed to collect an image frame (~550 msec). As noted above, this scheme leads to an oversampling of data, for which only half is used to recover the desired optical signal.

By ignoring the redundant data collected in step 225, the desired optical and hemodynamic signals are recovered by normalizing the measured response at each wavelength to a baseline value (e.g., an average over a selected time interval), and applying to them the inverse of the mathematical transformations used in step 215 (Step 230).

Graph 235 is an example of the wavelength-dependent driving voltage functions computed in step 220. The low frequency portion (1.8-20 Hz)) of graph 235 shows how the opacity of the LC cell 105 is varied depending on wavelength. The low amplitude portion 237 corresponds to a wavelength of 760 nanometers, and the high amplitude portion 236 corresponds to 830 nanometers. The high frequency portion of the graph 235 (oscillations within the low amplitude portion 237 or within the high amplitude portion 236) is provided as a mechanism to extend the life of the LC cell 105. In one embodiment, the period of the high and low amplitude portions is constant. In other embodiments, the period of the high and low amplitude portions can vary.

In a preferred embodiment, twisted nematic LC technology is implemented as the basis for electronically modulating the optical properties of the LC cell 105. Normally, LC cells 105 of this type are not wavelength selective, thus rendering it difficult to accurately mimic desired tissue optical responses (e.g., hemodynamic responses). To overcome this limitation, the opacity of the LC cell 105 is modulated in time such that at one time the opacity is appropriate for a selected illuminating wavelength and at another time it is appropriate for some other illuminating wavelength. When combined, the two (or more) selected opacities provide the attenuation properties that would be obtained had a cell been used that actually contained, for example, hemoglobin of a specified oxygenation level and concentration.

In the case of a two-wavelength illumination scheme this approach leads to the collection of temporal pairs of tomographic data for each considered value of hemoglobin. Appropriate adjustments to the LC cell opacity values can be made to provide for collection of a time-series of responses that mimic, for example, the response corresponding to hypoxemia, venous congestion, or any other hemodynamic response.

Figure 3:
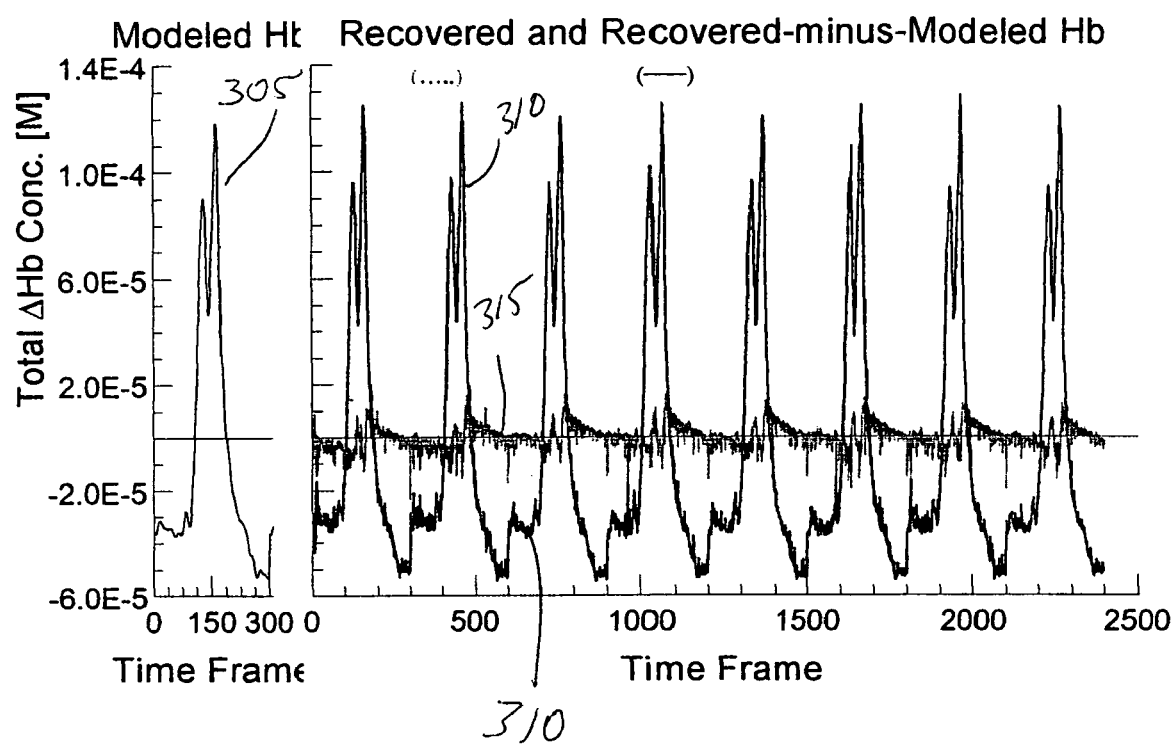
FIG. 3 is an illustrative plot of modeled and observed test functions mimicking a blood volume change, and recovery error, according to one embodiment of the invention.

Referring to FIG. 3, in one embodiment, an illustrative plot of modeled and observed test functions mimicking a blood volume change, and recovery error is shown. The solid curve 305 is the selected model function, which in this example reflects the change in total hemoglobin level seen when performing a Valsalva maneuver (venous congestion). The curve 310 shows the response derived for an optical transmission measurement performed on the laboratory bench, for eight consecutive replicates of the model dynamics, using the temporal opacity adjustment scheme just described applied to the considered LC cell technology. Inspection reveals that the response is highly repeatable. The difference between modeled and observed values is plotted as curve 315 that fluctuates about zero, indicating that the modeled and measured behaviors are nearly coincident.

Figure 4:
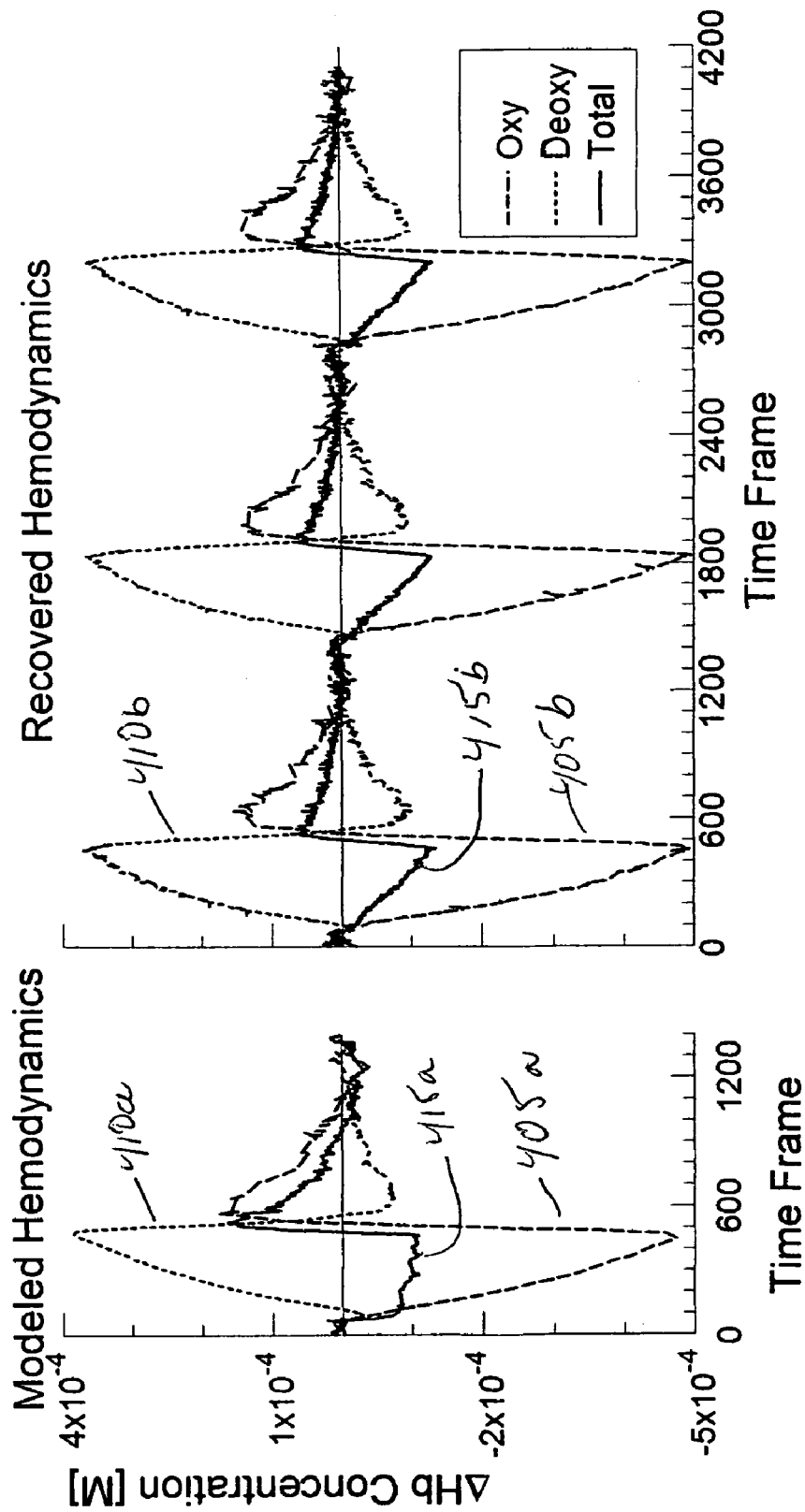
FIG. 4 is an illustrative plot of a modeled response to cuff ischemia, and measured response to three consecutive trials using an EC cell, according to one embodiment of the invention.

Referring to FIG. 4, in one embodiment, a modeled response to cuff ischemia, and measured response to three consecutive trials using an EC cell is shown. In this example, the hemodynamic response seen during acute limb ischemia produced in response to inflation of a pressure cuff, followed by its release and associated reactive hyperemia is shown. This maneuver produces a prompt decline in the level of oxyhemoglobin (shown by graph 405*a*), followed by its rapid increase upon reperfusion, a substantially opposite response for deoxyhemoglobin (shown by graph 410*a*) and a modest change in total hemoglobin levels (shown by graph 415*a*). The "Recovered Hemodynamics" plot shows the response obtained using the same temporal opacity adjustment scheme outlined above, for three consecutive cycles of the modeled behavior. As with the results shown in FIG. 3, the results shown in FIG. 4 demonstrate that the considered hemodynamic response can be accurately mimicked with excellent repeatability and fidelity, as shown in graphs 405*b*, 410*b*, and 415*b*.

Figure 5:
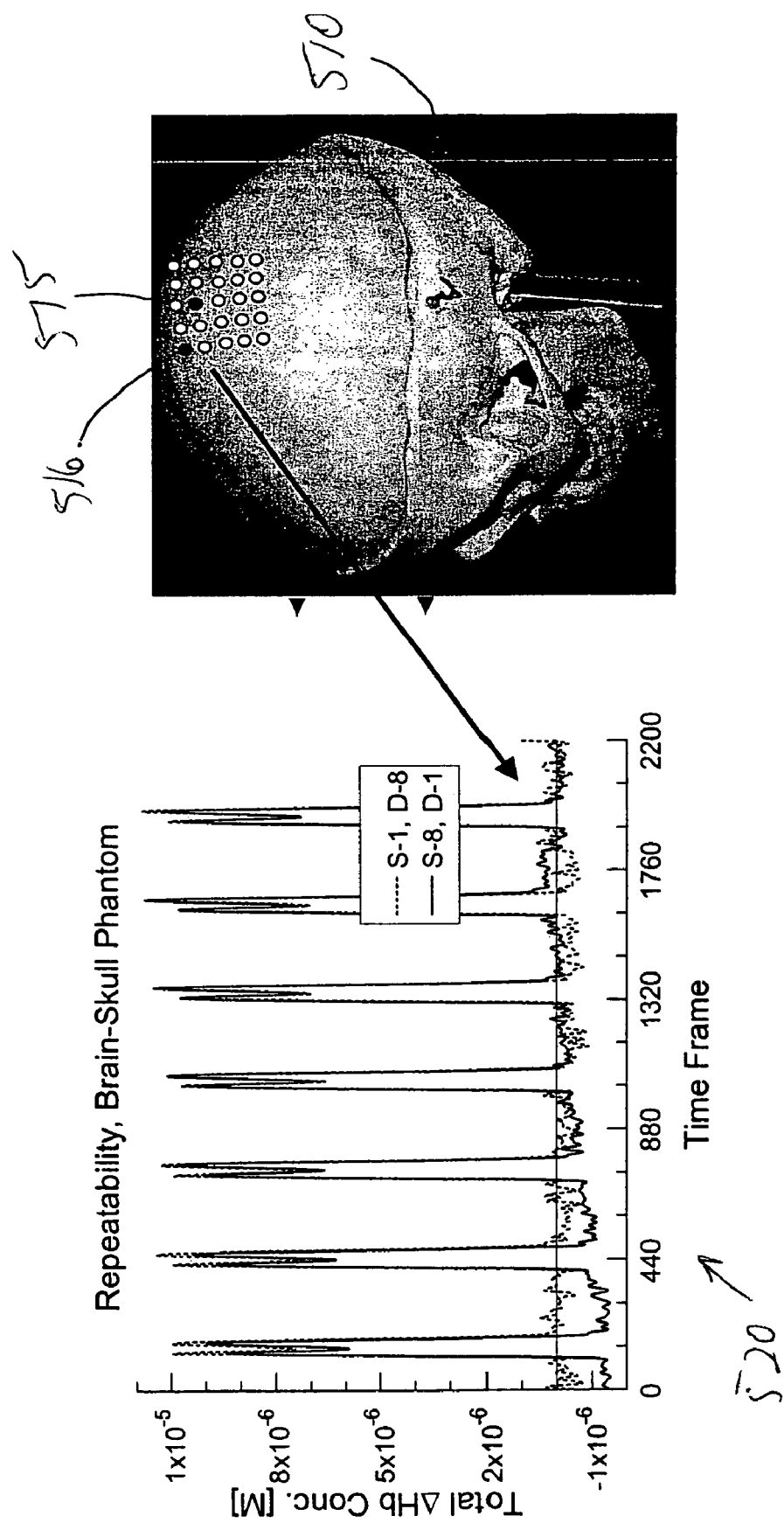
FIG. 5 is an illustrated plot of Measured Hb total changes mimicked using an LC cell embedded in human head phantom without the skull.

Referring to FIG. 5, in one embodiment, shown is a response obtained using the temporal opacity adjustment scheme applied to an LC cell 105 embedded in a head-like skull phantom 510 composed of absorbing and scattering materials that closely match the known optical properties of a real head. The phantom contains cerebral cortex molded from anatomical model and overlying clear CSF space. The depth of the LC cell 105 (not shown) is ~1 cm below surface of the skull. The background $\mu_a=0.04$ cm$^{-1}$; $\mu_s=7$ cm$^{-1}$. The array of dots 515 indicate the position of an array of optical fibers 110, as shown in FIG. 1C. The dark dots 516 indicate the position of illustrated measuring sites from reciprocal channels. Each array fiber includes a transmitter/receiver pair. Each member in the transmitter/receiver pair is capable of transmitting and receiving optical energy. When one member transmits, the other receives, and vice versa.

Figure 6:
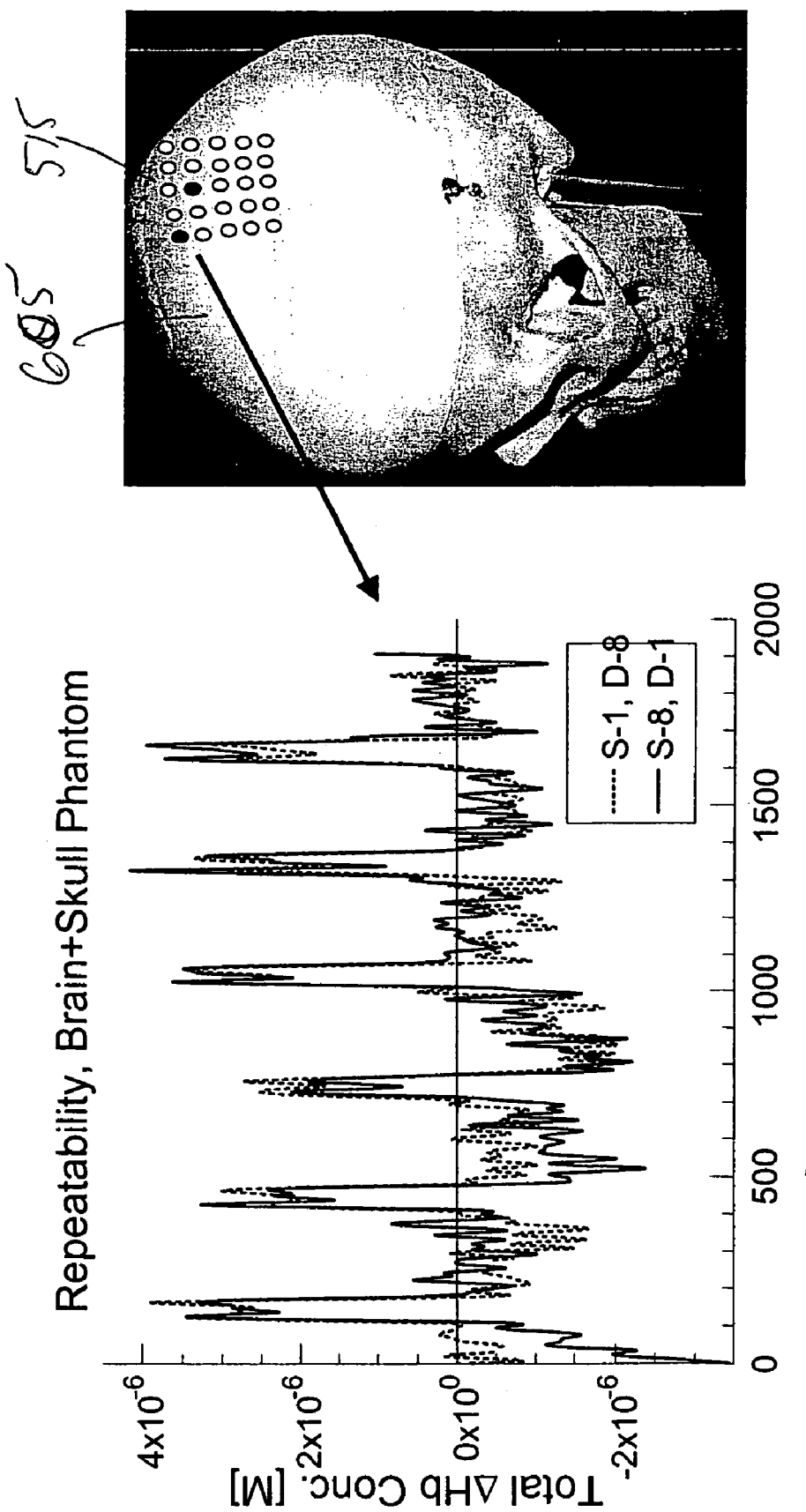
FIG. 6 is an illustrated plot of Measured Hb total changes mimicked using an LC cell embedded in head phantom minus skull, as shown in FIG. 4, except with the skull in place.

Referring to the graph in FIG. 5, in one embodiment, a graph 520 of the response of a reciprocal pair of illumination-detection fibers that comprise a subset of a larger 5×5 array of illuminating fibers 515 is shown. Inspection of the graph 520 in FIG. 5 reveals that even when the LC cell 105 is embedded in a surrounding scattering media, the Valsalva response can still be accurately mimicked with high repeatability, as seen in FIG. 3. In FIG. 6 a graph 620 of a similar response is shown, except an overlying skull 605 is included to mimic more accurately an actual response from a human subject. Repeatability of the considered response is evident, albeit with a higher noise level.

Figure 7B:
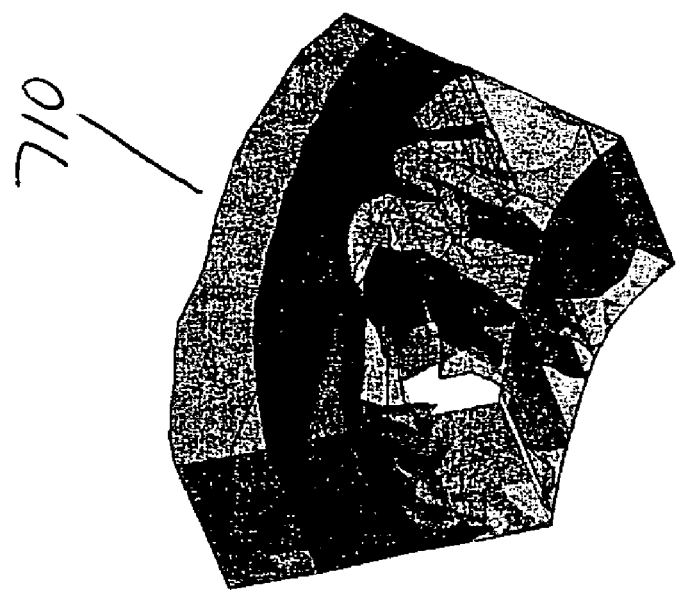
FIG. 7B is an illustrative volume rendered image showing the location of dynamic inclusion embedded in gray matter.
Figure 7A:
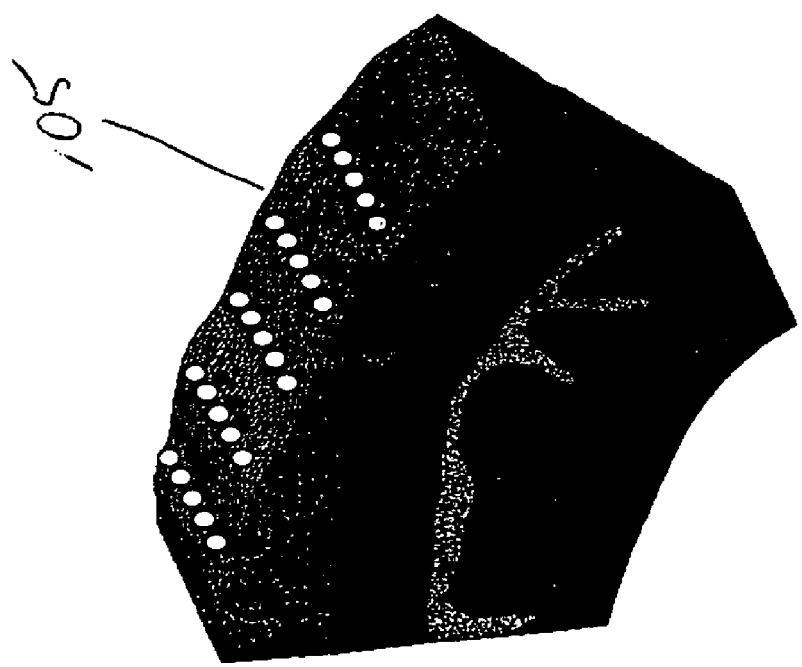
FIG. 7A is an illustrative segmented magnetic resonance brain map containing indicated tissue types.
Figure 7C:
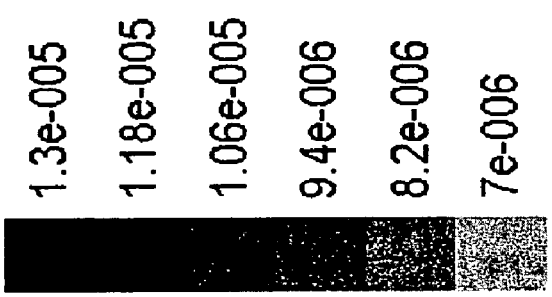
FIG. 7C is an illustrative diagram of a Brain Phantom with Skull and a three-dimensional reconstructed total hemoglobin (GLM) image.
Figure 7C:
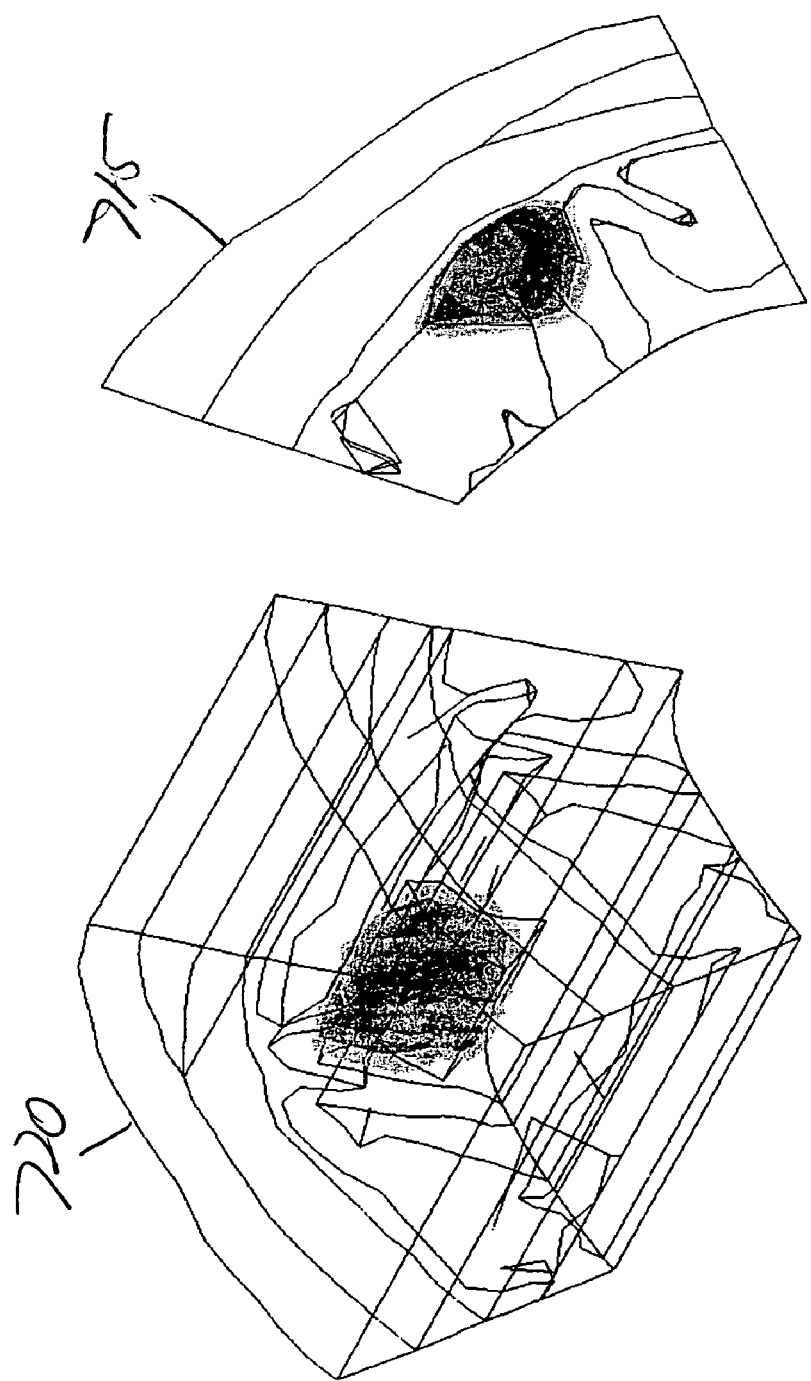

Referring to FIGS. 7A-C, in one embodiment, FIG. 7A is an illustrative segmented magnetic resonance brain map 705 containing indicated tissue types, FIG. 7B is an illustrative a volume rendered image 710 showing the location of dynamic inclusion embedded in gray matter, and FIG. 7C is an illustrative diagram of a brain phantom with skull 715 and a three-dimensional reconstructed total hemoglobin (GLM) image 720.

FIGS. 7A-C show the results obtained when the acquired time-series optical array data illustrated in FIG. 6 is subjected to image reconstruction using the Normalized Difference Method of Pei et al. (Pei, H. L. Graber, R. L. Barbour, "Influence of systematic errors in reference states on image quality and on stability of derived information for DC optical imaging," Applied Optics, Vol. 40, pp. 5755-5769 (2001)) and additionally processed to produce a volumetric image of the considered temporal behavior via a general linear model computation. For the considered case, the finite element mesh employed was derived from a magnetic resonance scan prior to the motor cortex area, which is the same area explored in the head phantom and is illustrated in a surface (FIG. 7A) and volume rendering (FIG. 7B). Comparison of the latter to results (FIG. 7C) shows that the considered hemodynamic response can be accurately recovered.

Figure 8:
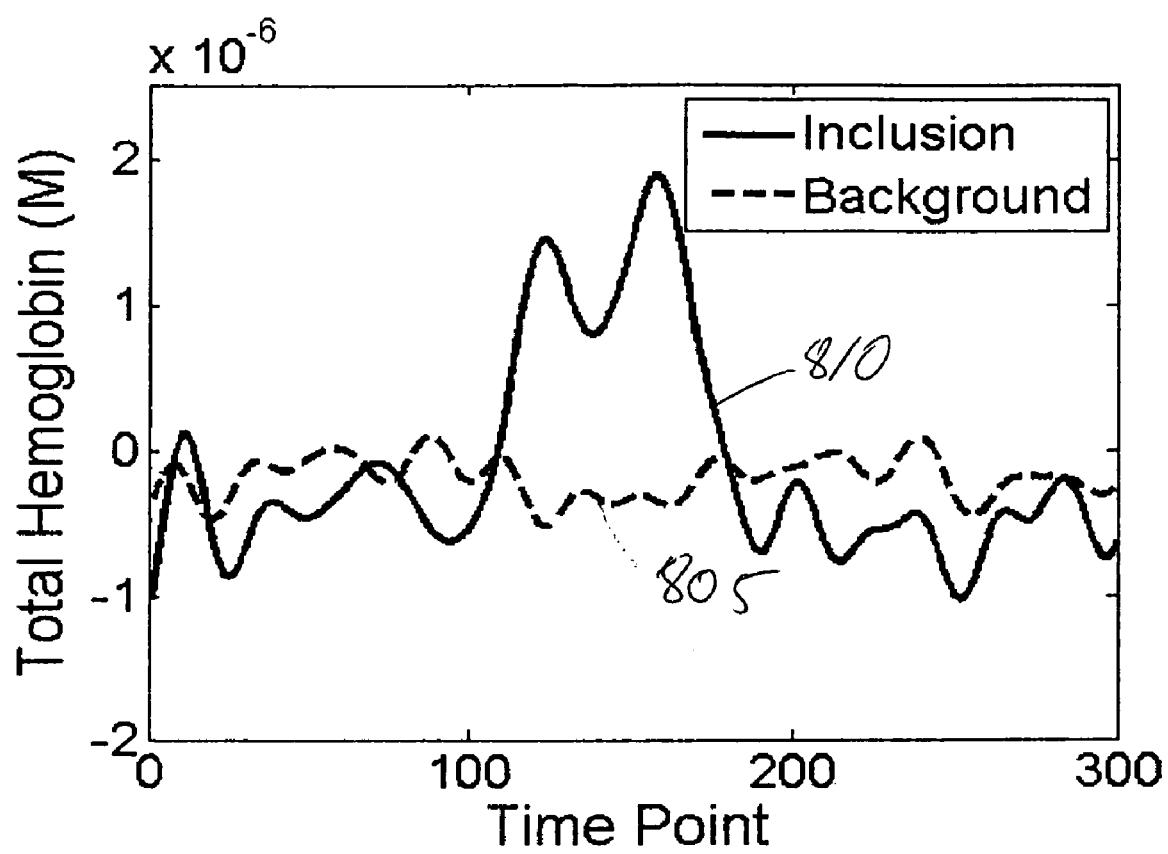
FIG. 8 is an illustrative graph of pixel time response of an LC cell (inclusion) and background.

Referring to FIG. 8, an illustrative graph of pixel time response of an LC cell 105 (inclusion) and background is shown. FIG. 8 shows the pixel response seen within the identified volume shown in FIG. 7C. Inspection reveals that compared to the image background (dotted line 805), the Valsalva response is clearly evident (solid line 810).

Whereas the considered temporal opacity adjustment scheme can be employed to provide for accurate mimicking of desired hemodynamic (or other) responses, it is evident to those skilled in the art that other approaches can be adopted to accomplish a similar end, particularly when applied to a two-dimensional array of LC cells. One example is a spatial encoding scheme wherein one LC pixel is coated with a thin-film optical material that permits light in one wavelength region to pass and not another. A different optical coating can be applied to an adjacent LC pixel thus only allowing light having a different wavelength range to pass. Because light is intensely scattered in materials that mimic the optical properties of tissue, in the limit of small sized cells, detection of spatial separation among adjacent LC cells embedded in tissue-like media is not possible thus rendering them to function as a single cell that has wavelength selective properties. Appropriate adjustment of the LC cell array size, optical coatings and driving currents can thus be used to obtain essentially any time-varying optical response.

In other considerations involving LC cell technology, it is also understood by those skilled in the art that a wide range of modifying materials can be added either directly to the LC medium to produce different optical effects (e.g., scattering, fluorescence, bioluminescence, etc.,), or to an adjacent cell. For instance, one could consider a sandwich arrangement wherein between two LC cells (e.g., one sensitive to absorbance changes, the other to scattering changes) are positioned in a cell containing a fluorescent material(s). This cell could be sealed thereby acting as an in situ fluorophore, or serve as a flow cell wherein materials of interest are exposed to light having desired properties. Such an arrangement could be used to model realistic light intensities in tissue that would be obtained in the case of, for instance, photodynamic therapy. In this fashion the considered dynamic phantom approach provides a quantitative means to evaluate the efficacy of new photosensitive materials having-potential therapeutic benefits. A similar consideration can be adopted in the case of bioluminescence or fluorescent radiative transfer mechanisms thereby permitting the mimicking of a wide range of optical effects.

It is also understood that the considered dynamic phantom approach using LC cell 105 or other considered electrochromic technologies can be adapted for use with a wide range of illumination and detection schemes. This includes, but is not limited to, use of AC optical illumination-detection schemes operating in the RF range or use of ultra-fast (fsec) light sources with fast detectors (streak camera). It is also understood that the considered approaches can be adopted for use in energy conversion schemes involving acoustic radiation (e.g., photo-acoustic imaging, acoustic modulation of light imaging). Also understood is that the considered temporal, spatial and optical modulation schemes described herein applied to LC cell technology can be applied to the mentioned EC technologies and those involving nanoparticles or even opto-acoustic cells.

In another embodiment, the invention involves a method of calibrating an instrument configured to execute time-series energy measurements of a target's response to incident energy. The method includes providing an electro-active device that is configured be electronically modulated to control the electro-active device's opacity. The electro-active device is embedded in a dense scattering medium. The method further includes selecting for the target, a known time dependent response pattern, and at least one associated coefficient value corresponding to a known physical property and determining at least one wavelength of energy that produces the known time-dependent response pattern for the known physical property of the target. The method further includes computing a wavelength-dependent driving voltage function by normalizing the at least one wavelength to a voltage response of the electro-active device, and applying a voltage to the electro-active device according to the wavelength-dependent driving voltage function to electrically modulate the electro-active device and thereby vary the opacity of the electro-active device. The method further includes synchronizing the instrument with the wavelength-dependent voltage driving function, transmitting energy at the at least one wavelength to the scattering medium and receiving scattered energy from the scattering medium, determining, based on the received scattered energy, a time-dependent response pattern for the target, and comparing the known time-dependent response pattern and the determined time-dependent response pattern.

In various embodiments, the energy includes optical or acoustic energy. In other embodiments, the electro-active device includes a twisted nematic liquid crystal that includes a dye coating to vary the optical properties of light transmitted through the liquid crystal.

Variations, modifications, and other implementations of what is described herein may occur to those of ordinary skill in the art without departing from the spirit and scope of the invention. Accordingly, the invention is not to be defined only by the preceding illustrative description.

What is claimed is:

1. A method of calibrating an instrument configured to execute time-series energy measurements of a target's response to incident energy, the method comprising:
   providing an electro-active device that is configured to be electronically modulated to control the electro-active device's opacity, the electro-active device being embedded in a dense scattering medium;

selecting, for a target, a known time-dependent response pattern and at least one associated coefficient value corresponding to a known physical property;

generating a time series of image frames by measuring a plurality of responses from said target to incident energy at a plurality of measurement wavelengths, wherein opacity of said electro-active device is adjusted for each image frame in said time series to correspond to all contributions due to selected measurement wavelength;

computing a wavelength-dependent driving voltage function by normalizing said time series to a desired voltage response range of said electro-active device at each of said plurality of measurement wavelengths;

applying a voltage to the electro-active device according to the wavelength-dependent driving voltage function to electrically modulate the electro-active device and thereby vary the opacity of the electro-active device;

synchronizing the instrument with the wavelength-dependent voltage driving function;

transmitting energy at said plurality of wavelengths to the scattering medium and receiving scattered energy from the scattering medium;

determining, based on the received scattered energy, a time-dependent response pattern for the target; and comparing the known time-dependent response pattern and the determined time-dependent response pattern.

2. The method of claim 1 wherein the energy comprises optical energy.

3. The method of claim 1 wherein the energy comprises acoustic energy.

4. The method of claim 1 wherein the electro-active device comprises a twisted nematic liquid crystal.

5. The method of claim 4 wherein the twisted nematic liquid crystal comprises a dye coating to vary the optical properties of light transmitted though the liquid crystal.

6. The method of claim 1 wherein the electro-active device comprises an electro-chromic polymer.

7. The method of claim 1 wherein the dense scattering medium comprises human tissue.

8. A method of calibrating an optical tomographic imaging system that is configured to execute time-series optical measurements of a target's response to incident optical energy, the method comprising:

providing an electro-active device that is configured to be electronically modulated to control the electro-active device's opacity, the electro-active device being embedded in a dense scattering medium;

selecting, for a target, a known hemodynamic response pattern and at least one associated coefficient value corresponding to a known optical property of the target;

generating a time series of linage frames by measuring a plurality of responses from said target to incident energy at a plurality of measurement wavelengths, wherein opacity of said electro-active device is adjusted for each image frame in said time series to correspond to all contributions due to selected measurement wavelength;

computing a wavelength-dependent driving voltage function by normalizing said time series to a desired voltage response range of said electro-active device at each of said plurality of measurement wavelengths;

applying a voltage to the electro-active device according to the wavelength-dependent driving voltage function to electrically modulate the electro-active device and thereby vary the opacity of the electro-active device;

synchronizing an image framing rate of the optical tomographic imaging system with the wavelength-dependent voltage driving function;

transmitting optical energy at the at least one wavelength to the scattering medium and receiving scattered optical energy from the scattering medium;

determining, based on the received scattered optical energy, a hemodynamic response for the target; and comparing the known hemodynamic response pattern and the determined hemodynamic response pattern.

9. The method of claim 8 wherein the electro-active device comprises a twisted nematic liquid crystal.

10. The method of claim 9 wherein the twisted nematic liquid crystal comprises a dye coating to vary the optical properties of light transmitted through the liquid crystal.

11. The method of claim 8 wherein the electro-active device comprises an electro-chromic polymer.

12. The method of claim 8 wherein the dense scattering medium comprises human tissue.

13. A system of calibrating an optical tomographic imaging system that is configured to execute time-series optical measurements of a target's response to incident optical energy, the system comprising:

an electro-active device that is configured to be electronically modulated to control the electro-active device's opacity, the electro-active device being embedded in a dense scattering medium;

means for selecting, for a target, a known hemodynamic response pattern and at least one associated coefficient value corresponding to a known optical property of the target;

means for generating a time series of image frames by measuring a plurality of responses from said target to incident energy at a plurality of measurement wavelengths, wherein opacity of said electro-active device is adjusted for each image frame in said time series to correspond to all contributions due to selected measurement wavelength;

means for computing a wavelength-dependent driving voltage function by normalizing said time series to a desired voltage response range of said electro-active device at each of said plurality of measurement wavelengths;

means for applying a voltage to the electro-active device according to the wavelength-dependent driving voltage function to electrically modulate the electro-active device and thereby vary the opacity of the electro-active device;

means for synchronizing an image framing rate of the optical tomographic imaging system with the wavelength-dependent voltage driving function;

means for transmitting optical energy at the at least one wavelength to the scattering medium and receiving scattered optical energy from the scattering medium;

means for determining, based on the received scattered optical energy, a hemodynamic response for the target; and means for comparing the known hemodynamic response pattern and the determined hemodynamic response pattern.

14. The system of claim 13 wherein the electro-active device comprises a twisted nematic liquid crystal.

15. The system of claim 14 wherein the twisted nematic liquid crystal comprises a dye coating to vary the optical properties of light transmitted through the liquid crystal.

16. The system of claim 13 wherein the electro-active device comprises an electro-chromic polymer.

17. The system of claim 13 wherein the dense scattering medium is human tissue.

18. A program storage device readable by a machine, tangibly embodying a program of instructions executable by the machine to perform method steps for calibrating an optical tomographic imaging system that is configured to execute time-series optical measurements of a target's response to incident optical energy, the method steps comprising:

providing an electro-active device that is configured to be electronically modulated to control the electro-active device's opacity, the electro-active device being embedded in a dense scattering medium;

selecting, for a target, a known hemodynamic response pattern and at least one associated coefficient value corresponding to a known optical property of the target;

generating a time series of image frames by measuring a plurality of responses from said target to incident energy at a plurality of measurement wavelengths, wherein opacity of said electro-active device is adjusted for each image frame in said time series to correspond to all contributions due to selected measurement wavelength;

computing a wavelength-dependent driving voltage function by normalizing said time series to a desired voltage response range of said electro-active device at each of said plurality of measurement wavelengths;

applying a voltage to the electro-active device according to the wavelength-dependent driving voltage function to electrically modulate the electro-active device and thereby vary the opacity of the electro-active device;

synchronizing an image framing rate of the optical tomographic imaging system with the wavelength-dependent voltage driving function;

transmitting optical energy at the at least one wavelength to the scattering medium and receiving scattered optical energy from the scattering medium;

determining, based on the received scattered optical energy, a hemodynamic response for the target; and comparing the known hemodynamic response pattern and the determined hemodynamic response pattern.

* * * * *